(12) United States Patent
Liu et al.

(10) Patent No.: US 11,760,709 B2
(45) Date of Patent: Sep. 19, 2023

(54) METHOD FOR PREPARING RESORCINOL THROUGH MICRO-CHANNEL REACTION

(71) Applicant: Inner Mongolia Sheng Tang International Mongolian Medicine Research Institute Co., Ltd., Inner Mongolia (CN)

(72) Inventors: Weidong Liu, Inner Mongolia (CN); Yantao Hao, Inner Mongolia (CN); Guodong Liang, Inner Mongolia (CN); Qinqin Gao, Inner Mongolia (CN); Pengshuai Li, Inner Mongolia (CN); Ting Zhang, Inner Mongolia (CN)

(73) Assignee: INNER MONGOLIA SHENG TANG INTERNATIONAL MONGOLIAN, Inner (CN)

( * ) Notice: Subject to any disclaimer, the term of this patent is extended or adjusted under 35 U.S.C. 154(b) by 20 days.

(21) Appl. No.: 17/329,650

(22) Filed: May 25, 2021

(65) Prior Publication Data
US 2022/0119330 A1    Apr. 21, 2022

(30) Foreign Application Priority Data
Oct. 19, 2020   (CN) .......................... 202011116527.2

(51) Int. Cl.
*C07C 37/045* (2006.01)
*C07C 245/20* (2006.01)
*C07C 37/05* (2006.01)

(52) U.S. Cl.
CPC ............ *C07C 37/045* (2013.01); *C07C 37/05* (2013.01); *C07C 245/20* (2013.01); *C07C 2601/16* (2017.05)

(58) Field of Classification Search
CPC .......................... C07C 37/045; C07C 245/20
See application file for complete search history.

(56) References Cited

U.S. PATENT DOCUMENTS

2004/0011650 A1* 1/2004 Zenhausern ........... B82Y 15/00
                                                                204/547

FOREIGN PATENT DOCUMENTS

| CN | 106905096 A | * | 6/2017 | ........... C07C 37/045 |
| CN | 110511117 A | * | 11/2019 | ........... C07C 37/002 |

(Continued)

*Primary Examiner* — Rosalynd A Keys
(74) *Attorney, Agent, or Firm* — Chun-Ming Shih; LANWAY IPR SERVICES

(57) ABSTRACT

The present disclosure provides a method for preparing resorcinol through micro-channel reaction. In the method, resorcinol is prepared through micro-channel reaction using m-aminophenol as a raw material, a diazo salt is synthesized at 0° C. or more, hydrolysis of the diazo salt is performed at 90° C. or less, and then reaction conditions are reduced; the reaction time is decreased from traditional 10 hours to less than 2 minutes, and therefore the reaction time is significantly shortened; the purity of a product is 75% or more, which is significantly improved. The method provided by the present disclosure has high heat exchange efficiency and high mass transfer rate; the efficiency of reaction is improved by hundreds of times; the reaction system is precisely controlled in the temperature and pressure, and safe and reliable in process, and meanwhile is capable of stably controlling hazard processes such as diazotization, so as to promote safe industry production, reduce energy consumption and greatly reduce industrial hazard waste emission and realize green ecology development.

8 Claims, 1 Drawing Sheet

(56) References Cited

FOREIGN PATENT DOCUMENTS

| CN | 110818533 A | * | 2/2020 | ............ | C07C 245/20 |
| CN | 111592447 A | * | 8/2020 | ............ | C07C 245/20 |

\* cited by examiner

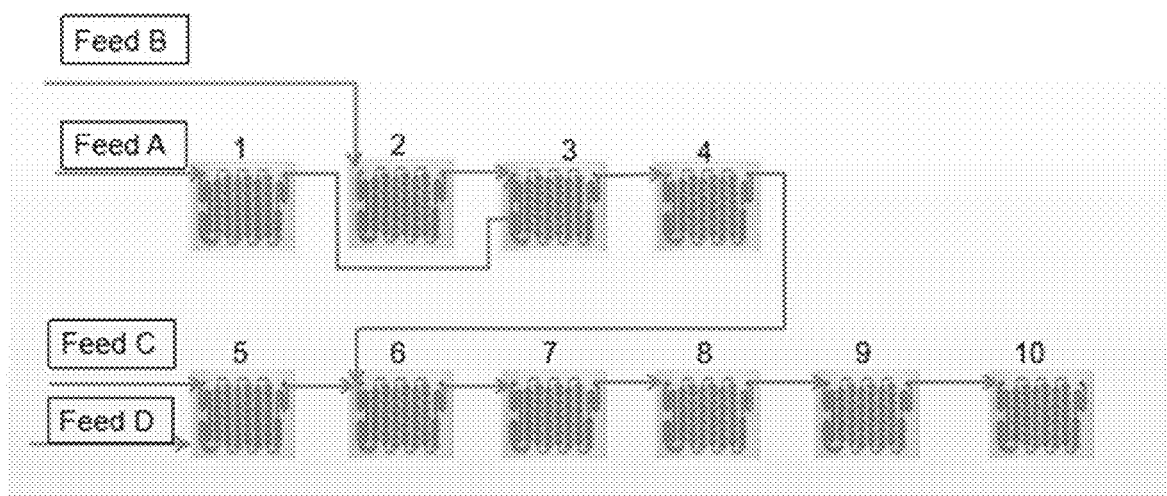

METHOD FOR PREPARING RESORCINOL THROUGH MICRO-CHANNEL REACTION

TECHNICAL FIELD

The present disclosure belongs to the technical field of medicine and chemical industry, and particularly relates to a method for preparing resorcinol through micro-channel reaction.

BACKGROUND

In the existing technology, preparation of resorcinol uses a m-aminophenol as a raw material, is realized through a batch kettle, and generally includes preparation of a diazo salt, hydrolysis of the diazo salt and recovery of a solvent. Since preparation of resorcinol from m-aminophenol uses a traditional batch kettle facility, preparation of the diazo salt in the reaction needs to be performed below 0° C.; heat is acutely released when in the hydrolysis reaction and lots of gases are generated; the existing technology has high production energy consumption, high process safe risk and low automation degree. The diazotization process is a hazard chemical process catalog which is major supervised for the first batch, is multiple in safety protection equipment, violent in reaction and uneasy control in temperature and stirring, the diazo salt enters into the next reaction behind time within the short period of time in order to maintain low temperature (below 0° C.), and a large amount of side reactions easily occur to affect the yield. Since reaction heat cannot be removed to cause too long dripping time, increased side reactions, stretched production period, high diazo compound reaction activity, multiple byproducts, difficult separation, large organic extraction solvent amount and incontinuous production, the existing technology has low yield, is not suitable for industrial production and is also difficultly used for preparing high-quality resorcinol.

SUMMARY

In order to solve the above technical problems, the present disclosure adopts a micro-channel reactor to synthesize resorcinol from m-aminophenol. In the method provided by the present disclosure, reaction conditions are easily implemented, the reaction period is greatly shortened and the yield is significantly improved.

The object of the present disclosure is to provide a method for preparing resorcinol through micro-channel reaction.

Provided is a method for preparing resorcinol through micro-channel reaction, comprising the following steps:

(1) preparation of a diazo salt: mixing m-aminophenol with sulfuric acid aqueous solution to obtain a first mixture, then conveying the first mixture to a first reaction module in a micro-reactor to be pre-cooled to 5~15° C.;

conveying the sodium nitrite aqueous solution to a second reaction module in the micro-reactor to be pre-cooled to 5~15° C.

conveying pre-cooled materials obtained in the first reaction module and the second reaction module to a third reaction module in the micro-reactor to be mixed and reacted, wherein the temperature of the third reaction module is 5~30° C., then conveying the above obtained mixture to a fourth reaction module in the micro-reactor to keep reacting to obtain a m-aminophenol diazo salt, wherein the temperature of the fourth reaction module is 5~30° C.;

(2) hydrolysis of the diazo salt: respectively conveying butyl acetate and water to a fifth reaction module in the micro-reactor to be preheated to 60~90° C., then conveying the preheated material to a sixth reaction module in the micro-reactor, and meanwhile conveying the m-aminophenol diazo salt obtained in step (1) to the sixth reaction module to be mixed to obtain a hydrolysis reaction mixture, wherein the temperature of the sixth reaction module is 60~90° C., conveying the hydrolysis reaction mixture to a seventh reaction module for hydrolysis reaction, wherein the temperature of the hydrolysis reaction is 60~90° C., finally conveying the resulting hydrolysis reactant to a cooling module to be cooled, and collecting a product to obtain the resorcinol.

In the present disclosure, m-aminophenol is used as a raw material. Firstly, m-aminophenol reacts with sodium nitrite aqueous solution in sulfuric acid solution having a low concentration to obtain a diazo salt, and then hydrolysis of the diazo salt is performed to obtain resorcinol. The synthesis routine is as follows:

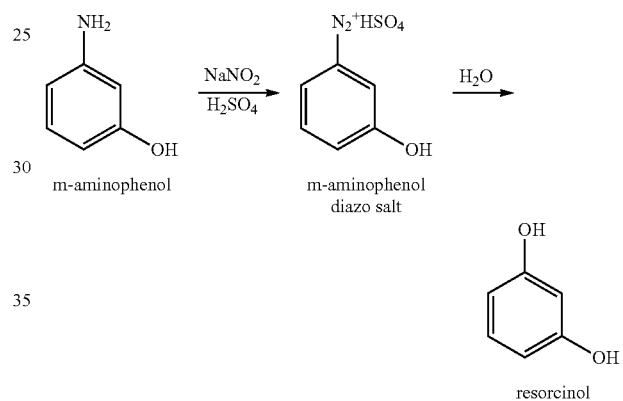

The present disclosure is performed through the micro-channel reactor. Compared with the traditional batch kettle, the content of the product in the obtained reaction mixed solution is significantly improved. Due to small liquid volume, high heat exchange efficiency, high mass transfer rate in the micro-channel reactor, the pressure of this exothermic reaction is stable, and the process is more safe and reliable. The preparation temperature of the diazo salt can be controlled at 0° C. or more in the process of reaction due to small liquid volume, high heat exchange efficiency, high mass transfer rate in the micro-channel reactor. And the temperature is controlled at 90° C. or less during the hydrolysis of the diazo salt, the reaction conditions are controllable and easily implemented, the energy consumption of the reaction is reduced, and the safety performance of the reaction is promoted; meanwhile the method provided by the present disclosure can reduce the generation of hazard byproducts, improves the purity and yield of the product and greatly reduces the hazard industrial emission so as to realize green ecological development. The method provided by the present disclosure can improve the purity of resorcinol by 75% or more, so it has broad application prospects.

Preferably, in step (1), the concentration of sulfuric acid solution is 20~35%. The diluted sulfuric acid having the above concentration is low viscosity and good mobility, can promote sufficient diazotization reaction and improve the yield of crude products, has low corrosivity and low equipment requirement, and is green and efficient. Further, the method of present application can reduce the dosage of sulfuric acid and cut down the waste liquid treatment costs Preferably, in step (1), a molar ratio of m-aminophenol to sulfuric acid solution is 1:2~3.5. In the present disclosure, m-aminophenol and sulfuric acid solution are matched based on the above molar ratio so that the obtained crude product is high in yield and high in purity.

Preferably, in step (1), the conveying rate of the first mixture is 0.02~12 kg/min.

In the present disclosure, reaction is performed in the micro-channel reactor, reaction parameters do not need to be changed from a trial to large-scale production, so the reactor is suitable for large-scale industrial production.

Preferably, in step (1), the conveying rate of the sodium nitrite aqueous solution is 0.012~6.79 kg/min.

Preferably, the concentration of the sodium nitrite aqueous solution is 20~40%, most preferably 36%. The conveying rate of the sodium nitrite aqueous solution depends on the conveying rate of the first mixture. The conveying rate of the sodium nitrite aqueous solution provided by the present disclosure can ensure that the molar ratio of sodium nitrite aqueous solution to m-aminophenol is within an optimal ratio range, thereby ensuring sufficient reaction.

Preferably, in step (1), a molar ratio of sodium nitrite to m-aminophenol is 0.95~1.2:1.

Preferably, in step (1), the reaction temperature of the third reaction module and the fourth reaction module are 5~30° C., and the reaction time is 15~40 s. The method provided by the present disclosure can ensure the rapid generation of the diazo salt. When the reaction temperature is 5~30° C. and the reaction time is 15~40 s, sufficient reaction can be ensured.

Preferably, in step (2), the purity of the organic solvent is 99.8% or more.

Preferably, in step (2), the organic solvent comprises one of ethyl acetate, n-butanol and n-butyl acetate, the conveying rate of the organic solvent is 0.0014~1159 kg/min, and the conveying rate of water is 0.003~3.09 kg/min.

Preferably, in step (2), a molar ratio of organic solvent to m-aminophenol is 6~9:1.

Preferably, in step (2), the time of hydrolysis reaction is 20~45 s.

The present disclosure has the beneficial effects:
1. In the method for preparing resorcinol through micro-channel reaction provided by the present disclosure, resorcinol is prepared by using m-aminophenol as a raw material through micro-channel reaction, and the diazo salt is synthesized at 0° C. or more, and hydrolysis of the diazo salt is performed at 90° C. or less, and reaction conditions are reduced; the reaction time is reduced from traditional about 10 hours to less than 2 minutes, and the reaction time is significantly shortened; the purity of the product is 75% or more, and the purity is greatly improved.
2. The method provided by the present disclosure has high heat exchange efficiency and high mass transfer rate; the efficiency of reaction is improved by hundreds of times; the reaction system is precisely controlled in the temperature and pressure, and safe and reliable in process, and meanwhile is capable of stably controlling hazard processes such as diazotization, so as to promote safe industry production, reduce enemy consumption and greatly reduce industrial hazard waste emission and realize green ecology development.

BRIEF DESCRIPTION OF THE DRAWINGS

For a better understanding of the embodiments of the present disclosure or the technical solution in the prior art, the drawings used in the embodiments or in the prior art will be simply discussed below, obviously, the drawings in the description below are only some Examples in the present disclosure. Persons of ordinary skill in the art can also obtain other drawings according to these drawings without creative efforts.

FIG. 1 is a flowchart of a feed reaction of a method for preparing resorcinol through micro-channel reaction provided by the present disclosure.

DESCRIPTION OF THE EMBODIMENTS

To make the purpose, the features and the benefits of the present disclosure more clear, the technical solution of the present disclosure will be described in detail. Obviously, the described Examples are only some Examples of the present disclosure but not all the Examples. Based on the Examples of the present disclosure, other implementation modes obtained by persons of ordinary skill in the art without creative efforts are all included within the scope of protection of the present disclosure.

The following examples of the present disclosure use Corning G1-10FM reactor (namely AFR®-G1-10FM reactor), four Corning pumps are used to convey materials, two Corning® heat exchangers are used to control the temperature of the reactor, and finally one module is cooled using air.

The present disclosure provides a method for preparing resorcinol through micro-channel reaction, comprising the following steps:
(1) preparation of a diazo salt: m-aminophenol with sulfuric acid aqueous solution having a concentration of 20~35% were mixed to obtain a first mixture, wherein a molar ratio of the m-aminophenol to sulfuric acid solution was 1:2~3.5, and the obtained first mixture was conveyed via a first feed pump (Feed A) at the conveying rate of 0.02~12 kg/min to a first reaction module in a G1 reactor to be pre-cooled to 5~15° C.;
sodium nitrite aqueous solution having a concentration of 20~40% was conveyed via a second feed pump (Feed B) at the conveying rate of 0.006~3.4 kg/min to a second reaction module in the G1 reactor to be pre-cooled to 5~15° C.;
the pre-cooled materials obtained in the first reaction module and the second reaction module were conveyed to a third reaction module in the micro-reactor to be mixed, wherein a molar ratio of sodium nitrite to m-aminophenol is 0.95~1.2:1, and the temperature of the third reaction module was 5~30° C. to react, the above obtained mixture was conveyed to a fourth reaction module in the micro-reactor to react to obtain a m-aminophenol diazo salt, wherein the temperature of the fourth reaction module was 5~30° C., and the reaction time was 15~40 s;
hydrolysis of the diazo salt: an organic solvent having a purity of 99.8% which was one of ethyl acetate, n-butanol and n-butyl acetate and water were respectively conveyed to a fifth reaction module via a third feed pump (Feed C) at the conveying rate of 0.0014~13.59 kg/min and via a fourth feed pump (Feed D) at the conveying rate of 0.003~3.09 kg/min to be preheated to 60~90° C., then the organic solvent was conveyed via the third feed pump, the water was conveyed via the fourth feed pump, and meanwhile the m-aminophenol diazo salt obtained in step (1) was conveyed to a sixth reaction module to be mixed to obtain a hydrolysis reaction mixture, a molar ratio of the organic solvent to the diazo salt is 6~9:1, the temperature of the sixth reaction module was 60~90V, the hydrolysis reaction mixture was conveyed to a seventh reaction module to react and flowed through an eighth reaction module and a ninth reaction module via the seventh reaction module for hydrolysis reaction, the temperatures from the seventh reaction module to the ninth reaction module were all maintained at 60~90° C., hydrolysis reaction time was 20~45 s, and then finally the resulting hydrolysis reactant was fed to a cooling module and finally flowed out of the reactor to enter into a collection tank to obtain the resorcinol.

The present disclosure provides the following examples and comparative examples, wherein examples 1~5 are seen in Table 1, examples 6~9 and comparative examples 1-2 are seen in Table 2, and examples 10~13 and comparative examples 3~4 are seen in Table 3.

TABLE 1

Parameters of examples 1~5

| Groups | Example 1 | Example 2 | Example 3 | Example 4 | Example 5 |
|---|---|---|---|---|---|
| Weight (g) of m-aminophenol | 281.2 | 365.5 | 281.2 | 365.5 | 281.2 |
| Concentration (%) of sulfuric acid | 30 | 30 | 30 | 30 | 30 |
| Molar ratio of m-aminophenol to sulfuric acid | 1:2.5 | 1:2.5 | 1:2.5 | 1:2.5 | 1:2.5 |
| Conveying rate (kg/min) of Feed A | 0.02 | 0.5 | 6 | 12 | 2 |
| Pre-cooling temperature (° C.) of first reaction module | 10 | 10 | 10 | 5 | 15 |
| Concentration (%) of sodium nitrite weight (g) | 528.5/26.6 | 635.5/26.6 | 513.7/26.6 | 644.87/26.6 | 528.5/26.6 |
| Conveying rate (kg/min) of Feed B | 0.006 | 0.5 | 3.4 | 1.0 | 0.06 |
| Pre-cooling temperature (° C.) of second reaction module | 10 | 10 | 10 | 5 | 15 |
| Molar ratio of sodium nitrite to m-aminophenol | 1.07:1 | 0.99:1 | 1.05:1 | 1.05:1 | 1.15:1 |
| Temperature (° C.) of third reaction module | 10 | 5 | 15 | 30 | 15 |
| Temperature (° C.) of fourth reaction module | 10 | 5 | 15 | 30 | 15 |
| Reaction time(s) of step (1) | 34.7 | 35.8 | 17.4 | 34.8 | 34.7 |
| Conveying rate (kg/min) of Feed C | 0.016 | 0.0014 | 13.59 | 2 | 0.15 |
| Conveying rate (kg/min) of Feed D | 0.005 | 0.02 | 1.05 | 3.09 | 2.84 |
| Temperature (° C.) of fifth reaction module | 60 | 90 | 80 | 80 | 60 |
| Varity of organic solvents | n-butyl acetate | Ethyl acetate | n-butanol | n-butyl acetate | n-butyl acetate |
| Molar ratio of organic solvent to m-aminophenol | 7.6:1 | 6.43:1 | 7.58:1 | 7.3:1 | 9:1 |
| Temperature (° C.) of sixth reaction module | 60 | 90 | 80 | 80 | 60 |
| Temperature (° C.) of hydrolysis reaction 水 | 60 | 90 | 80 | 80 | 60 |
| Hydrolysis time(s) | 40.4 | 43 | 22.6 | 40.5 | 45 |

Other variables of reactions in examples 6~9 and comparative examples 1-2 are the completely same, the difference is the concentration of sulfuric acid, wherein the concentrations of sulfuric acids in examples 6~9 and comparative examples 1-2 are seen in Table 2.

TABLE 2

Concentrations of sulfuric acids examples 6~9 and comparative examples 1~2

| Groups | Comparative Example 1 | Example 6 | Example 7 | Example 8 | Example 9 | Comparative Example 2 |
|---|---|---|---|---|---|---|
| Amount of sulfuric acid | 2.5 eq | 2.5 eq | 2.5 eq | 2.5 eq | 2.5 eq | 2.5 eq |
| Concentration of sulfuric acid | 15 | 20 | 25 | 30 | 35 | 40 |

Other variables in reactions in examples 10~13 and comparative examples 3~4 are the completely same and the difference is the molar ratio of m-aminophenol to sulfuric acid, specifically see in Table 3.

TABLE 3

Partial parameters of examples 10~13 and comparative examples 3~4

| Groups | Comparative Example 3 | Example 10 | Example 11 | Example 12 | Example 13 | Comparative Example 4 |
|---|---|---|---|---|---|---|
| Amount of m-aminophenol | 1.0 eq | 1.0 eq | 1.0 eq | 1.0 eq | 1.0 eq | 1.0 eq |
| Amount of sulfuric acid | 1.5 eq | 2.0 eq | 2.5 eq | 3.0 eq | 3.5 eq | 4.0 eq |

Test Example m-aminophenol (reaction solution) obtained in examples 1~13 and comparative examples 1~4 is detected using high performance liquid chromatography. Specific detection conditions are as follows:

Flow velocity: 0.8 mL/min
Chromatographic column C18 4.6×250 mm (Shimadzu C18 4.6×250 mm Chromatographic column)
Detection wavelength: 274 nm
Column temperature: 30° C.
Flowing phase: A phase: water: B phase: methanol
Loading amount: 10 μL 1. 100 g of resorcinol reaction products (reaction solution) obtained from step (2) in examples 1~5 were extracted respectively for later use, and then diluted by 5000 folds. Purity detection was performed using Shimadzu high performance liquid chromatograph. Results are seen in Table 4.

TABLE 4

Purity detection results of resorcinol obtained in examples 1~5

| Groups | Example 1 | Example 2 | Example 3 | Example 4 | Example 5 |
|---|---|---|---|---|---|
| Purity (%) | 82.0 | 75.0 | 79.24 | 78.04 | 75.14 |

It can be seen from Table 4 that in the preparation method of the new continuous flow micro-channel process for diazotization and hydrolysis of resorcinol provided by the present disclosure, the preparation time is within two minutes, the purity of the obtained resorcinol is 75% or more, the preparation period is short, the preparation efficiency is high, and the purity of the obtained product is high.

2. 100 g of resorcinol reaction products (reaction solution) obtained from step (2) in examples 6~9 and comparative examples 1-2 were respectively taken to detect the purity of the reaction solution, and the purity and yield of the crude product. Results are seen in Table 5.

TABLE 5

Detection results of examples 6~9 and comparative examples 1~2

| | Amount of sulfuric acid | Concentration of sulfuric acid | Purity of reaction solution | Purity of crude product | Amount of crude product | Yield of crude product |
|---|---|---|---|---|---|---|
| Comparative example 1 | 2.5 eq | 15% | 69.2% | 81.2% | 4.9 g | 44.5% |
| Example 6 | 2.5 eq | 20% | 80.1% | 97.9% | 6.3 g | 57.3% |
| Example 7 | 2.5 eq | 25% | 81.3% | 98.5% | 6.4 g | 58.2% |

TABLE 5-continued

Detection results of examples 6~9 and comparative examples 1~2

| | Amount of sulfuric acid | Concentration of sulfuric acid | Purity of reaction solution | Purity of crude product | Amount of crude product | Yield of crude product |
|---|---|---|---|---|---|---|
| Example 8 | 2.5 eq | 30% | 80.3% | 98.4% | 6.3 g | 57.3% |
| Example 9 | 2.5 eq | 35% | 79.7% | 99.6% | 5.9 g | 53.6% |
| Comparative example 2 | 2.5 eq | 40% | 58.7% | 76.5% | 3.6 g | 32.7% |

It can be seen from results in Table 5 in that in examples 6~9, the concentration of sulfuric acid is between 20% and 35%, the purity of the obtained reaction solutions is 79.7% or more, the purity of the crude products is 98.4% or more, the yield of the crude products is 53.6% or more; when the concentration of sulfuric acids is 15%, the purity of the obtained reactions solution is 69.2%, the purity of the crude products is 81.2%, the yield of the crude products is 44.5%; when the concentration of sulfuric acid is 40%, the purity of the reaction solution is 58.7%, the yield of the crude product is 76.5%, and the yield of the crude product is 32.7%. Accordingly, when the concentration of sulfuric acid is less than 20% or more than 35%, the purity and yield of the obtained resorcinol are seriously affected.

3. 100 g of resorcinol reaction products (reaction solution) obtained from step (2) in examples 10~13 and comparative examples 3~4 were respectively taken to detect the purity of the reaction solution, and the purity and yield of the crude product. Results are seen in Table 6.

TABLE 6

Detection results of examples 10~13 and comparative examples 3~4

| | Amount of m-aminophenol | Concentration of sulfuric acid | Purity of reaction solution | Purity of crude product | Amount of crude product | Yield of crude product |
|---|---|---|---|---|---|---|
| Comparative example 3 | 1.0 eq | 1.5 eq | 70.1% | 89.2% | 5.1 g | 46.3% |
| Example 10 | 1.0 eq | 2.0 eq | 75.6% | 99.2% | 5.5 g | 50.0% |
| Example 11 | 1.0 eq | 2.5 eq | 78.2% | 98.9% | 6.4 g | 58.2% |
| Example 12 | 1.0 eq | 3.0 eq | 80.4% | 98.9% | 6.5 g | 59.1% |
| Example 13 | 1.0 eq | 3.5 eq | 80.6% | 98.7% | 6.4 g | 58.2% |
| Comparative example 4 | 1.0 eq | 4.0 eq | 65.3% | 82.5% | 4.2 g | 38.1% |

It can be seen from results in Table 6 in that when the molar ratio of m-aminophenol to sulfuric acid is between 1:2 and 3.5, the purity of the reaction solution is 75.6% or more, the purity of the crude product is 98.7% or more, the yield of the crude product is 50% or more; when the molar ratio of m-aminophenol to sulfuric acid is less than 1:3.5 or more than 1:2, the purity and yield of the crude product are greatly reduced, which indicates that the m-aminophenol and sulfuric acid provided by the present disclosure within the above ranges can effectively improve the yield and purity of the crude product.

The above descriptions are only embodiments of the present disclosure, however, the protective scope of the present disclosure is not limited to thereto. Any persons of skill in the art can easily conceive that changes or replacements within the technical scope disclosed in the present disclosure should be included within the protective scope of the present, disclosure. Therefore, the protective scope of the present disclosure shall be subject to the protective scope of the claims.

What is claimed is:

1. A method for preparing resorcinol through microchannel reaction, comprising the following steps:
    (1) preparation of a diazo salt:
        mixing m-aminophenol with sulfuric acid aqueous solution to obtain a first mixture, then conveying the first mixture to a first reaction module in a micro-reactor to be pre-cooled to 5~15° C., wherein the concentration of the sulfuric acid solution is 20~35%, and a molar ratio of the m-aminophenol to the sulfuric acid solution is 1:2~3.5;
        conveying sodium nitrite aqueous solution to a second reaction module in the micro-reactor to be pre-cooled to 5~15° C.;
        conveying the pre-cooled materials obtained in the first reaction module and the second reaction module to a third reaction module in the micro-reactor to be mixed and reacted, wherein the temperature of the third reaction module is 5~30° C., then conveying the above obtained mixture to a fourth reaction module in the micro-reactor to react to obtain a m-aminophenol diazo salt, wherein the temperature of the fourth reaction module is 5~30° C.;
    (2) hydrolysis of the diazo salt:
        respectively conveying an organic solvent and water to a fifth reaction module in the micro-reactor to be preheated to 60~90° C., then conveying the above preheated material to a sixth reaction module in the micro-reactor, and meanwhile conveying the m-aminophenol diazo salt obtained in step (1) to the sixth reaction module to be mixed to obtain a hydrolysis reactant, wherein the temperature of the sixth reaction module is 60~90° C., conveying the hydrolysis reactant to a seventh reaction module for further hydrolysis reaction, wherein the temperature of the hydrolysis reaction is 60~90° C., finally conveying the above obtained hydrolysis reactant to a cooling module to be cooled, and collecting a product to obtain the resorcinol,
    wherein the first reaction module is independent from the second reaction module, and the fourth reaction module is independent from the fifth reaction module.

2. The method for preparing resorcinol through microchannel reaction according to claim 1, wherein in step (1), the conveying rate of the first mixture is 0.02~12 kg/min.

3. The method for preparing resorcinol through microchannel reaction according to claim 1, wherein in step (1), the conveying rate of the sodium nitrite solution is 0.012~6.79 kg/min.

4. The method for preparing resorcinol through microchannel reaction according to claim 1, wherein in step (1), a molar ratio of sodium nitrite to m-aminophenol is 0.95~1.2:1.

5. The method for preparing resorcinol through microchannel reaction according to claim 1, wherein in step (1), the reaction temperature of the fourth reaction module is 5~30° C., and the reaction time is 15~40 s.

6. The method for preparing resorcinol through microchannel reaction according to claim 1, wherein in step (2), the organic solvent comprises one of ethyl acetate, n-butanol and n-butyl acetate, the conveying rate of the organic solvent is 0.0014~13.59 kg/min, and the conveying rate of water is 0.003~3.09 kg/min.

7. The method for preparing resorcinol through microchannel reaction according to claim 1, wherein in step (2), a molar ratio of organic solvent to m-aminophenol diazo salt is 6~9:1.

8. The method for preparing resorcinol through microchannel reaction according to claim 1, wherein in step (2), the time of hydrolysis reaction is 20~45 s.

* * * * *